US012357372B2

(12) United States Patent
Kingsley et al.

(10) Patent No.: US 12,357,372 B2
(45) Date of Patent: Jul. 15, 2025

(54) END EFFECTOR ASSEMBLY FOR USE IN A ROBOTIC SURGICAL INSTRUMENT

(71) Applicant: Covidien LP, Mansfield, MA (US)

(72) Inventors: Dylan R. Kingsley, Broomfield, CO (US); Crystal A. Adams, Westminster, CO (US); Jason G. Weihe, Longmont, CO (US); William R. Whitney, Boulder, CO (US); Russell W. Holbrook, Longmont, CO (US); Zachary S. Heiliger, Nederland, CO (US); Curtis M. Siebenaller, Frederick, CO (US)

(73) Assignee: Covidien LP, Mansfield, MA (US)

( * ) Notice: Subject to any disclaimer, the term of this patent is extended or adjusted under 35 U.S.C. 154(b) by 524 days.

(21) Appl. No.: 16/998,024

(22) Filed: Aug. 20, 2020

(65) Prior Publication Data
US 2022/0054190 A1 Feb. 24, 2022

(51) Int. Cl.
*A61B 18/14* (2006.01)
*A61B 18/00* (2006.01)
*A61B 34/37* (2016.01)
*A61B 90/00* (2016.01)

(52) U.S. Cl.
CPC .......... *A61B 18/1445* (2013.01); *A61B 34/37* (2016.02); *A61B 90/03* (2016.02); *A61B 2018/00077* (2013.01); *A61B 2018/00601* (2013.01); *A61B 2090/035* (2016.02)

(58) Field of Classification Search
CPC ................................................ A61B 18/1445
See application file for complete search history.

(56) References Cited

U.S. PATENT DOCUMENTS

| 5,752,973 | A  | 5/1998  | Kieturakis      |
| 5,792,135 | A  | 8/1998  | Madhani et al.  |
| 5,848,986 | A  | 12/1998 | Lundquist et al.|
| 6,817,974 | B2 | 11/2004 | Cooper et al.   |
| 7,799,028 | B2 | 9/2010  | Schechter et al.|
| 7,861,906 | B2 | 1/2011  | Doll et al.     |
| 7,918,230 | B2 | 4/2011  | Whitman et al.  |
| 8,579,176 | B2 | 11/2013 | Smith et al.    |
| 9,055,961 | B2 | 6/2015  | Manzo et al.    |

(Continued)

FOREIGN PATENT DOCUMENTS

| EP | 2992838 A2 | 3/2016 |
| EP | 3338673 A1 | 6/2018 |

(Continued)

OTHER PUBLICATIONS

International Search Report and Written Opinion dated Nov. 16, 2021, issued in corresponding international application No. PCT/US2021/044590, 12 pages.

*Primary Examiner* — Mallika D Fairchild
*Assistant Examiner* — Thien Jason Tran

(57) ABSTRACT

An end effector assembly of a robotic surgical instrument includes a distal segment and first and second jaw members supported by the distal segment. The distal segment defines an elongate slot therein. The first jaw member has a proximal flange portion received in the elongate slot of the distal segment, and the second jaw member has a proximal flange portion received in the distal segment. The proximal flange portions of each of the first and second jaw member are pinned to the distal segment.

13 Claims, 5 Drawing Sheets

(56) References Cited

U.S. PATENT DOCUMENTS

| | | |
|---|---|---|
| 9,474,569 B2 | 10/2016 | Manzo et al. |
| 2002/0099371 A1 | 7/2002 | Schulze et al. |
| 2002/0177842 A1 | 11/2002 | Weiss |
| 2003/0125734 A1 | 7/2003 | Mollenauer |
| 2003/0208186 A1 | 11/2003 | Moreyra |
| 2006/0022015 A1 | 2/2006 | Shelton et al. |
| 2006/0025811 A1 | 2/2006 | Shelton |
| 2007/0233052 A1 | 10/2007 | Brock |
| 2007/0282358 A1 | 12/2007 | Remiszewski et al. |
| 2008/0015631 A1 | 1/2008 | Lee et al. |
| 2010/0274265 A1 | 10/2010 | Wingardner et al. |
| 2010/0292691 A1 | 11/2010 | Brogna |
| 2011/0118707 A1 | 5/2011 | Burbank |
| 2011/0118708 A1 | 5/2011 | Burbank et al. |
| 2011/0118709 A1 | 5/2011 | Burbank |
| 2011/0118754 A1 | 5/2011 | Dachs, II et al. |
| 2012/0215220 A1* | 8/2012 | Manzo .................. A61B 34/30 606/46 |
| 2014/0005663 A1* | 1/2014 | Heard ................ A61B 18/1445 606/41 |
| 2016/0066982 A1 | 3/2016 | Marczyk et al. |
| 2019/0321062 A1 | 10/2019 | Williams |
| 2020/0305904 A1* | 10/2020 | Holman .................. B23K 26/21 |
| 2020/0305956 A1* | 10/2020 | Behymer ........... A61B 17/2909 |
| 2021/0220000 A1* | 7/2021 | Heiliger ................ A61B 34/35 |

FOREIGN PATENT DOCUMENTS

| | | |
|---|---|---|
| EP | 3689282 A1 | 8/2020 |
| WO | 2016187006 A1 | 11/2016 |
| WO | 2017136710 A2 | 8/2017 |

* cited by examiner

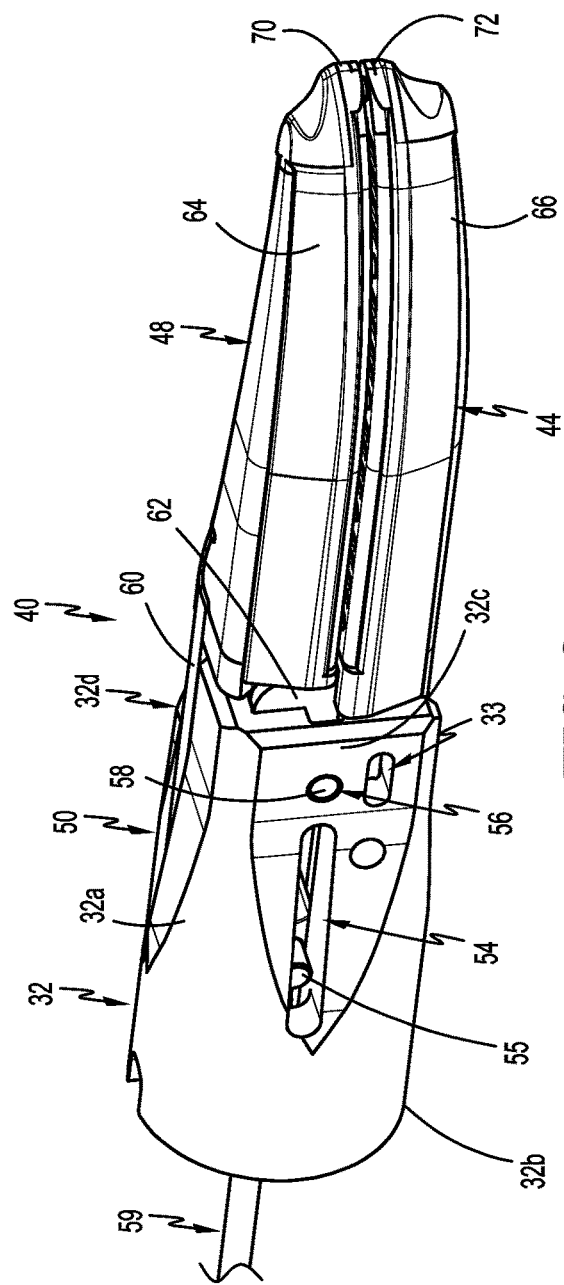
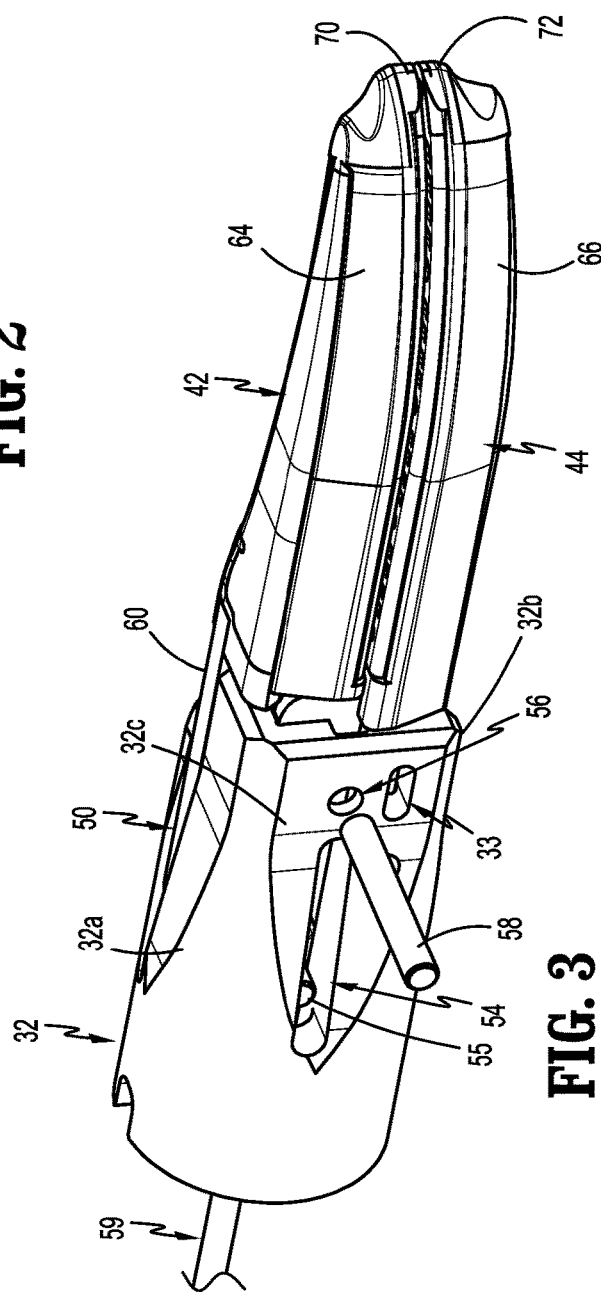

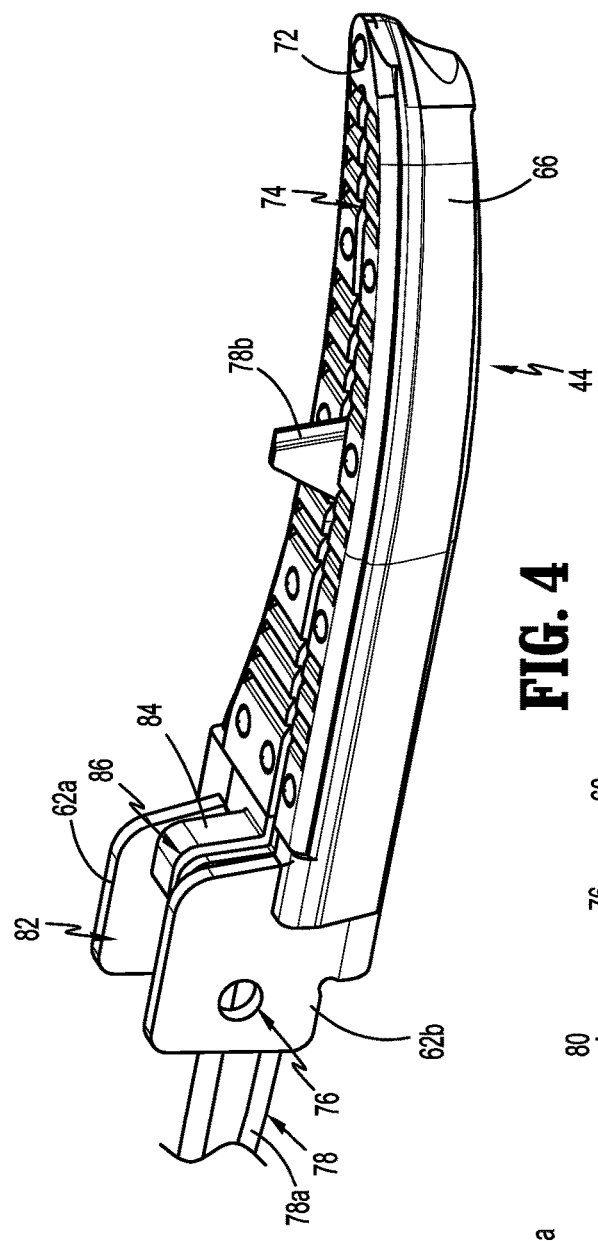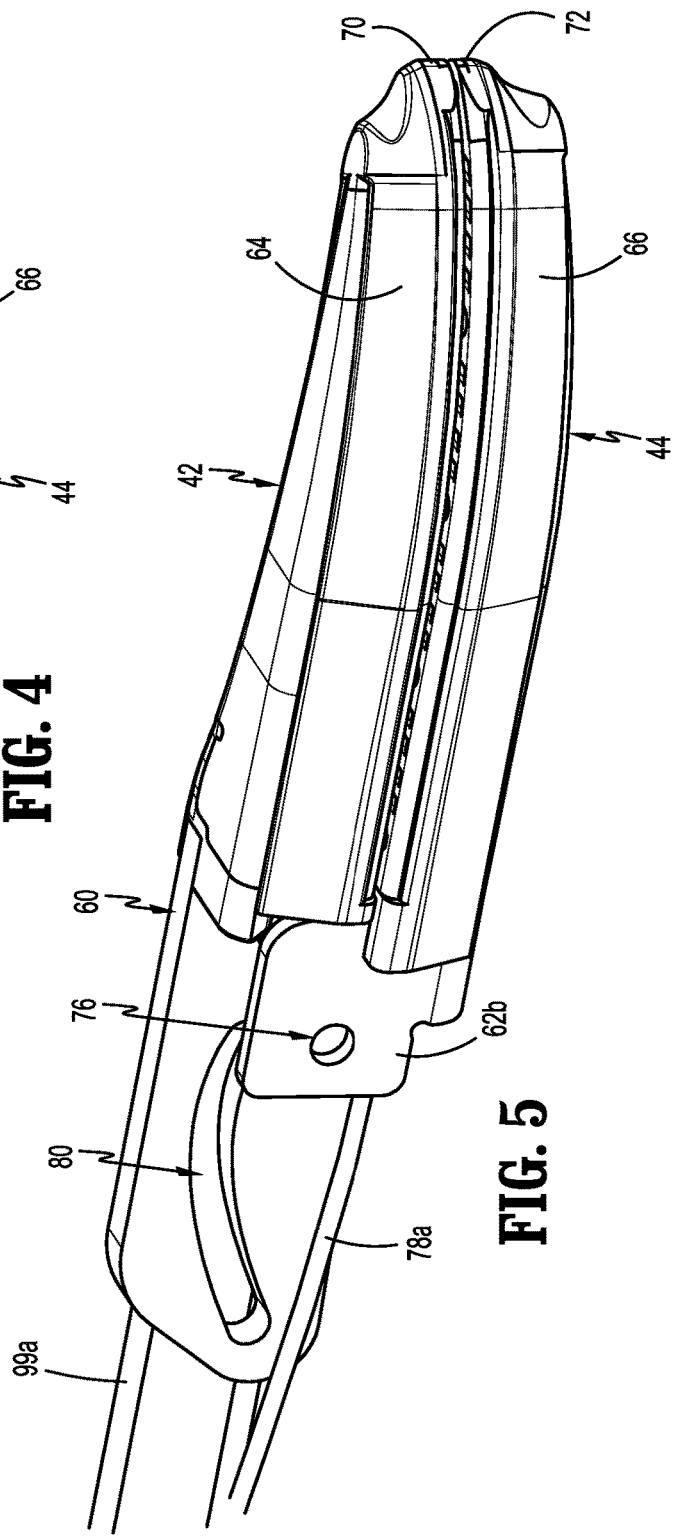
FIG. 4
FIG. 5

END EFFECTOR ASSEMBLY FOR USE IN A ROBOTIC SURGICAL INSTRUMENT

FIELD

The present disclosure relates to surgical instruments and, more specifically, to articulating end effector assemblies for use in robotic surgical systems.

BACKGROUND

Robotic surgical systems are increasingly utilized in various surgical procedures. Some robotic surgical systems include a console supporting a robotic arm. One or more different surgical instruments may be configured for use with the robotic surgical system and selectively mountable to the robotic arm. The robotic arm provides one or more inputs to the mounted surgical instrument to enable operation of the mounted surgical instrument.

The surgical instruments or portions thereof may be configured as single-use instruments or portions that are discarded after use, or may be configured as reusable instruments or portions that are cleaned and sterilized between uses. Regardless of the configurations of the surgical instruments, the console and robotic arm are capital equipment configured for long-term, repeated use. The console and robotic arm may be protected by a sterile barrier during use and/or wiped clean after use to ensure cleanliness for subsequent uses.

SUMMARY

As used herein, the term "distal" refers to the portion that is being described which is further from an operator (whether a human surgeon or a surgical robot), while the term "proximal" refers to the portion that is being described which is closer to the operator. The terms "about," "substantially," and the like, as utilized herein, are meant to account for manufacturing, material, environmental, use, and/or measurement tolerances and variations, and in any event may encompass differences of up to 10%. To the extent consistent, any of the aspects described herein may be used in conjunction with any or all of the other aspects described herein.

Provided in accordance with aspects of the present disclosure is an end effector assembly of a robotic surgical instrument. The end effector assembly includes a distal segment and first and second jaw members. The distal segment defines an elongate slot therein and has a side wall defining a linear slot and an opening. The opening is disposed distally of the linear slot. Each of the first and second jaw members includes a distal body portion and a proximal flange portion extending proximally from the respective distal body portion. The proximal body portion of the first jaw member is received in the elongate slot of the distal segment and defines an angled cam slot configured for receipt of a cam pin. The proximal flange portion of the second jaw member is received in the distal segment. The proximal flange portion of each of the first and second jaw members is pinned to the distal segment via the opening in the distal segment such that the first jaw member and/or the second jaw member is configured to pivot relative to the distal segment between a closed state and an open state. The first and second jaw members are closer to one another in the closed state than in the open state.

In aspects, the proximal flange portion of the second jaw member may include a first proximal flange portion, and a second proximal flange portion spaced laterally from the first proximal flange portion to define a gap between the first and second proximal flange portions. The proximal flange portion of the first jaw member may be disposed in the gap.

In aspects, the proximal flange portion of the first jaw member may extend further proximally than the proximal flange portion of the second jaw member.

In aspects, the distal segment may be configured to prevent rotation of the second jaw member relative to the distal segment.

In aspects, the end effector assembly may further include a cam bar having a distal end portion received in the distal segment. The distal end portion of the cam bar may support the cam pin thereon.

In aspects, the end effector assembly may further include a pivot pin received in the opening of the distal segment. The pivot pin may extend through the proximal flange portion of each of the first and second jaw members. The distal end portion of the cam bar may define an annular cutout configured to receive the pivot pin when the cam bar is in a distal position.

In aspects, the end effector assembly may further include a knife blade. The distal body portion of each of the first and second jaw members may define a longitudinally-extending knife channel configured for passage of the knife blade.

In aspects, the second jaw member may have a surface feature supported on a proximal end of the distal body portion of the second jaw member and protruding toward the first jaw member. The surface feature may define a slot having the knife blade received therein when the knife blade is in a proximal position.

In accordance with another aspect of the disclosure, a robotic surgical instrument is provided and includes a housing configured to be operably coupled to a surgical robotic arm, a shaft assembly extending distally from the housing, and an end effector assembly. The end effector assembly includes a distal segment coupled to a distal end portion of the shaft assembly and first and second jaw members. The distal segment is configured to articulate relative to the shaft assembly and has a side wall defining a linear slot, and an opening that is disposed distally of the linear slot. Each of the first and second jaw members includes a distal body portion and a proximal flange portion extending proximally from the respective distal body portion and received in the distal segment. The proximal body portion of the first jaw member defines an angled cam slot configured for receipt of a cam pin. The proximal flange portion of each of the first and second jaw members is pinned to the distal segment via the opening in the distal segment such that the first jaw member and/or the second jaw member is configured to pivot relative to the distal segment between a closed state and an open state. The first and second jaw members are closer to one another in the closed state than in the open state.

In aspects, the distal segment may define an elongate slot therein, and the proximal flange portion of the first jaw member may be received in the elongate slot.

In accordance with yet another aspect of the disclosure, a method of assembling an end effector assembly of a robotic surgical instrument is provided. The method includes: inserting a knife blade through a knife channel defined longitudinally through a first jaw member of an end effector assembly; positioning a second jaw member on the first jaw member; inserting a cam bar through a distal segment and coupling a distal end portion of the cam bar with the second jaw member; positioning the distal segment over the first and second jaw members; and inserting a pivot pin through each of the distal segment and the first and second jaw members.

In aspects, positioning the distal segment over the first and second jaw members may include inserting a proximal flange portion of one or both of the first and second jaw members into an elongate slot defined in the distal segment.

In aspects, inserting the cam bar may include positioning a cam pin of the cam bar into a cam slot defined in a proximal flange portion of at least one of the first or second jaw members.

In aspects, the method may further include guiding electric wires and a knife rod from the first and second jaw members proximally through the distal segment after inserting the cam bar.

BRIEF DESCRIPTION OF THE DRAWINGS

Various aspects and features of the present disclosure are described hereinbelow with reference to the drawings wherein:

FIG. 2 is a side perspective view illustrating an end effector assembly of the surgical instrument of FIG. 1;

FIG. 3 is a side perspective view of the end effector assembly of FIG. 2 illustrating a pivot pin separated from the end effector assembly;

FIG. 4 is a side perspective view illustrating a jaw member and a knife blade of the end effector assembly of FIG. 2;

FIG. 5 is a side perspective view illustrating first and second jaw members of the end effector assembly of FIG. 2;

DETAILED DESCRIPTION

Figure 1:
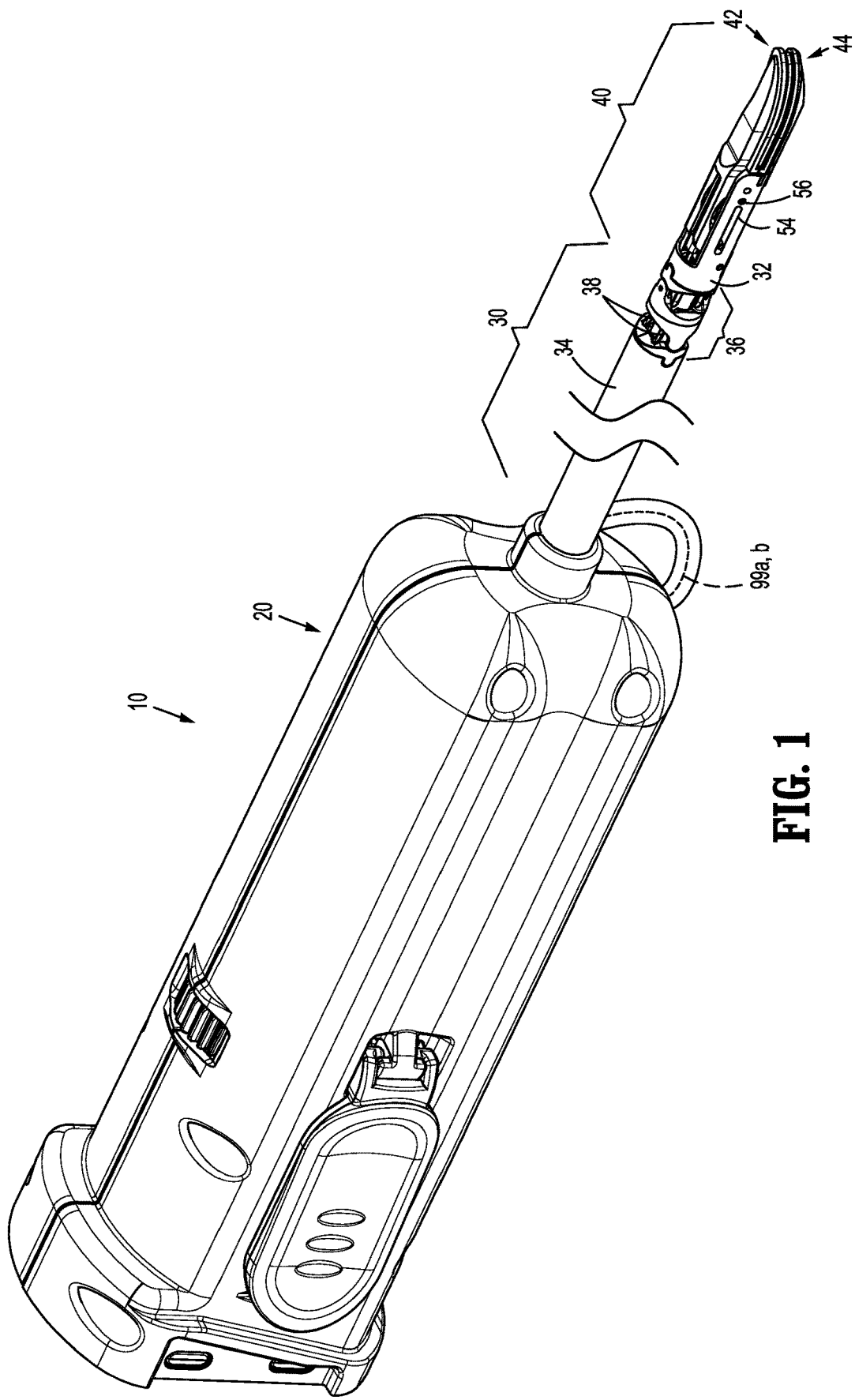
FIG. 1 is a perspective view of a surgical instrument provided in accordance with the present disclosure configured for mounting on a robotic arm of a robotic surgical system.
Figure 7:
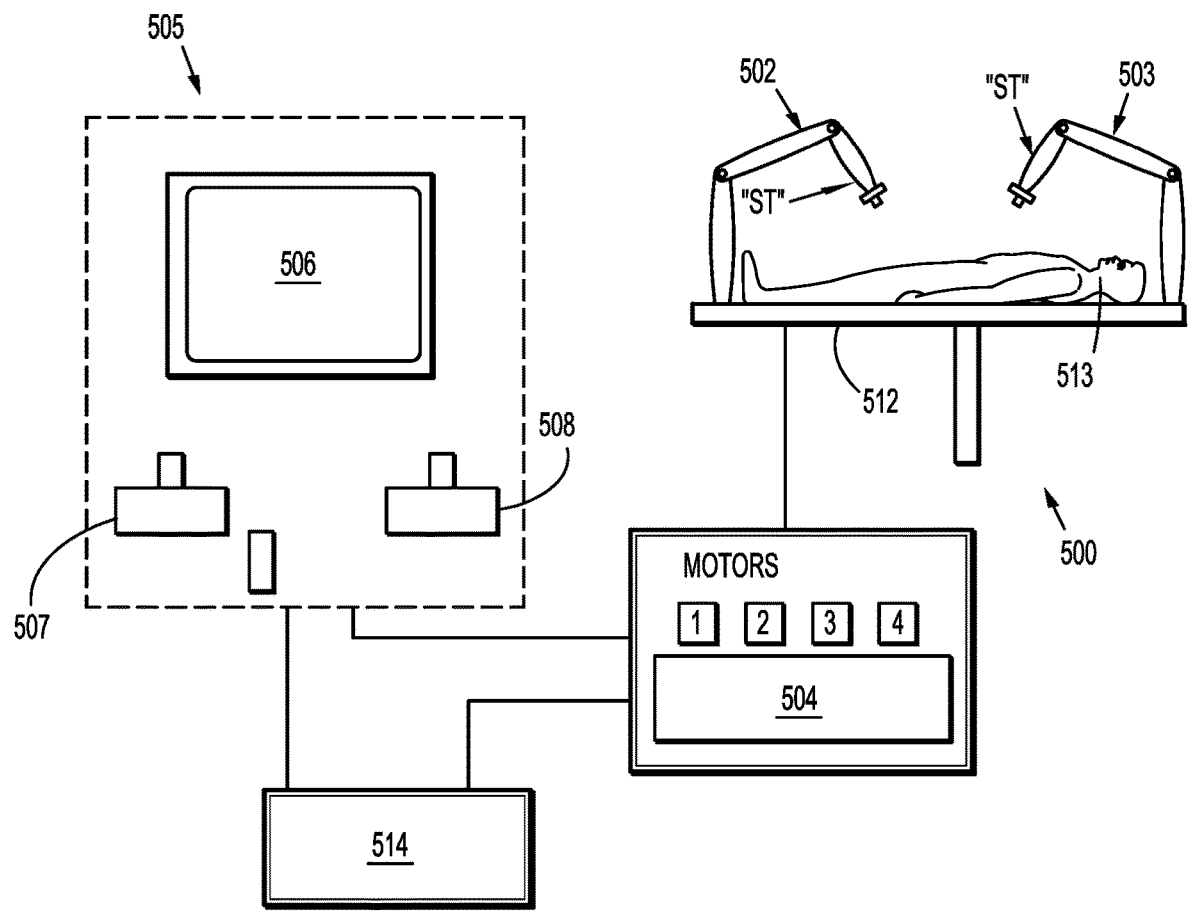
FIG. 7 is a schematic illustration of an exemplary robotic surgical system configured to releasably receive the surgical instrument of FIG. 1.

Referring to FIG. 1, a surgical instrument 10 provided in accordance with the present disclosure generally includes a housing 20, a shaft assembly 30 extending distally from housing 20, an end effector assembly 40 extending distally from shaft assembly 30, and an actuation assembly (not explicitly shown) disposed within housing 20 and operably associated with shaft assembly 30 and end effector assembly 40. Housing 20 of instrument 10 releasably engages with a robotic arm of a surgical system, e.g., robotic surgical system 500 (FIG. 7). Instrument 10 is detailed herein as an articulating electrosurgical forceps configured for use with a robotic surgical system, e.g., robotic surgical system 500 (FIG. 7). However, the aspects and features of instrument 10 provided in accordance with the present disclosure, detailed below, are equally applicable for use with other suitable surgical instruments and/or in other suitable surgical systems.

Shaft assembly 30 of instrument 10 includes a distal segment, such as, for example, a collar or clevis 32, a proximal segment 34, and an articulating section 36 disposed between the distal and proximal segments 32, 34. In aspects, the clevis 32 may alternatively form part of the end effector assembly 40. Articulating section 36 includes one or more articulating components, e.g., links, joints, etc. A plurality of articulation cables 38, e.g., four (4) articulation cables, or other suitable actuators, extends through articulating section 36. More specifically, articulation cables 38 are operably coupled to clevis 32 of shaft assembly 30 at the distal ends thereof and extend proximally from clevis 32 of shaft assembly 30, through articulating section 36 of shaft assembly 30 and proximal segment 34 of shaft assembly 30, and into housing 20, wherein articulation cables 38 operably couple with an articulation assembly (not explicitly shown) of the actuation assembly to enable selective articulation of clevis 32 (and, thus end effector assembly 40) relative to proximal segment 34 and housing 20, e.g., about at least two axes of articulation (yaw and pitch articulation, for example). Articulation cables 38 are arranged in a generally rectangular configuration, although other suitable configurations are also contemplated.

Figure 6:
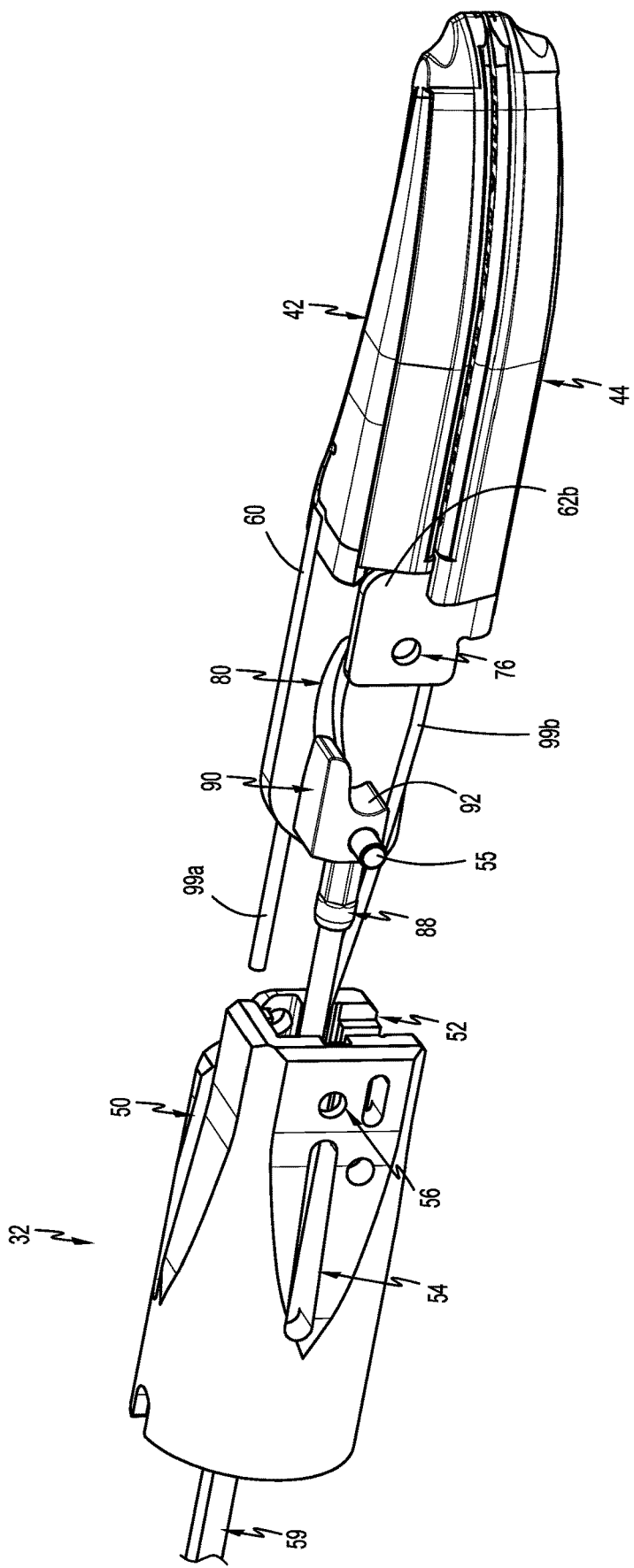
FIG. 6 is a side perspective view of the first and second jaw members of the end effector assembly of FIG. 2 with a clevis shown separated therefrom.

With reference to FIGS. 2, 3, and 6, clevis 32 includes first and second opposing upper and lower walls 32a, 32b and first and second opposing side walls 32c, 32d. Each of the upper and lower walls 32a, 32b defines a cut-out 50, 52 (FIG. 6) that extends proximally from a distal end of the clevis 32 and partially through the length of the clevis 32. The cut-outs 50, 52 are configured for receipt of a proximal flange portion 60 of a first jaw member 42 of end effector assembly 40, as will be described in further detail below. At least the first side wall 32c defines a slot 54 that extends transversely through a thickness of the first side wall 32c. The slot 54 is configured for slidable receipt of a cam pin 55 of a cam bar 59 to guide and support cam bar 59 as cam bar 55 translates between proximal and distal positions relative to clevis 32. At least the first side wall 32c of clevis 32 defines an opening 56 therein that is disposed distally of and aligned with linear slot 54. Opening 56 in first side wall 32c is configured for receipt of a pivot pin 58 that secures first and second jaw members 42, 44 to clevis 32.

With reference to FIGS. 2-6, as mentioned above, end effector assembly 40 includes first and second jaw members 42, 44, respectively. In aspects, clevis 32 may also be considered a component of end effector assembly 40. Each jaw member 42, 44 includes a proximal flange portion 60, 62 and a distal body portion 64, 66, respectively. Distal body portions 64, 66 define opposed tissue-contacting surfaces 70, 72, respectively. Tissue-contacting surfaces 70, 72 of jaw members 42, 44, respectively, are at least partially formed from an electrically conductive material and are energizable to different potentials to enable the conduction of electrical energy through tissue grasped therebetween, although tissue-contacting surfaces 70, 72 may alternatively be configured to supply any suitable energy, e.g., thermal, microwave, light, ultrasonic, etc., through tissue grasped therebetween for energy-based tissue treatment. Instrument 10 defines a conductive pathway (not shown) through housing 20 and shaft assembly 30 to end effector assembly 40 that may include electric lead wires 99a, 99b (FIGS. 1 and 6), contacts, and/or electrically-conductive components to enable electrical connection of tissue-contacting surfaces 70, 72 of jaw members 42, 44, respectively, to an energy source (not shown), e.g., an electrosurgical generator via an electrosurgical cable extending therebetween, for supplying energy to tissue-contacting surfaces 70, 72 to treat, e.g., seal, tissue grasped between tissue-contacting surfaces 70, 72.

With reference to FIGS. 4-6, tissue-contacting surfaces 70, 72 each define a longitudinally-extending knife channel 74 (only knife channel 74 of second jaw member 44 is explicitly shown, FIG. 4). A knife assembly 78 is provided that includes a knife rod 78a and a knife blade 78b fixed to or otherwise coupled to a distal end of knife rod 78a. The knife rod 78a extends from housing 20 through shaft assembly 30 to end effector assembly 40. Knife blade 78b is disposed within end effector assembly 40 between jaw members 42, 44 and is provided to enable cutting of tissue grasped between tissue-contacting surfaces 70, 72 of jaw members 42, 44, respectively. Knife rod 78a is operably coupled to a knife drive assembly (not explicitly shown) of the actuation assembly of the housing 20 to enable selective actuation thereof to, in turn, reciprocate the knife blade 78b between jaw members 42, 44 (and through knife channels 74) to cut tissue grasped between tissue-contacting surfaces 70, 72.

Proximal flange portions 60, 62 of respective first and second jaw members 42, 44 are pivotably coupled to one another about pivot pin 58 (FIG. 3). For example, each of proximal flange portions 60, 62 of first and second jaw members 42, 44 defines a pin hole 76 (only pin hole of proximal flange portion 62 is explicitly shown, FIGS. 4-6) transversely therethrough in which pivot pin 58 is received. Further, as mentioned above, pivot pin 58 extends through pin holes 56 in clevis 32 such that first and second jaw members 42, 44 are axially restrained to clevis 32 while being permitted to rotate or pivot relative to clevis 32. Proximal flange portion 60 of first jaw member 42 may have a plate-like, rectangular configuration and defines an angled or curved cam slot 80 extending along a length thereof. The cam slot 80 is configured for receipt of cam pin 55 of cam bar 59.

Proximal flange portion 62 of second jaw member 44 may include a pair of first and second proximal flange portions 62a, 62b that are laterally spaced from one another to define a gap 82 therebetween. The proximal flange portion 60 of first jaw member 42 is received in the gap 82. Second jaw member 44 may further include a knife guide feature 84, such as, for example, a protuberance, supported on a proximal end of the distal body portion 66 of the second jaw member 44. The knife guide feature 84 protrudes toward the first jaw member 42 and defines a slot 86 having the knife blade 78b received therein when the knife blade 78b is in a proximal, pre-deployed position. As such, knife blade 78b is safely concealed within knife guide feature 84 when in the proximal position.

With reference to FIG. 6, cam bar 59 of end effector assembly 40 includes a distal end portion 88 having a block 90, and the cam pin 55 extending outwardly from opposing lateral sides of block 90. Block 90 defines an annular cutout 92 configured to receive the pivot pin 58 (FIG. 3) when the cam bar 59 is in a distal, deployed position. The annular cutout 92, therefore, allows the full distal translation of the cam bar 59 without interference from the pivot pin 58. A first end of cam pin 55 is received in linear cam slot 54 of clevis 32 to guide and support a linear movement of cam bar 59, and a second end of cam pin 55 (not explicitly shown) is received in angled cam slot 80 of proximal flange portion 60 of first jaw member 42.

Cam slot 80 in proximal flange portion 60 of first jaw member 42 is shaped such that retraction (e.g., proximal translation) of cam bar 59 relative to proximal flange portion 60 causes the cam pin 55 to ride proximally through cam slot 80 and drive a pivoting of jaw member 42 toward second jaw member 44 to transition end effector assembly 40 from a spaced-apart position (e.g., an open position of end effector assembly 40) to an approximated position (e.g. a closed position of end effector assembly 40) for grasping tissue between tissue-contacting surfaces 70, 72. Similarly, advancement (e.g., distal translation) of cam bar 59 relative to proximal flange portion 60 causes cam pin 55 to ride distally through cam slot 80 and drive a pivoting of first jaw member 42 away from second jaw member 44 to transition end effector assembly 40 from the closed state to the open state. As an alternative to this unilateral configuration, a bilateral configuration may be provided whereby both jaw members 42, 44 are pivotable relative to one another and clevis 32 of shaft assembly 30. Additionally or alternatively, cam bar 59 may be moved distally to transition end effector assembly 40 to the approximated position and proximally to transition end effector assembly 40 to the spaced-apart position.

Cam bar 59 extends proximally from end effector assembly 40 through shaft assembly 30 and into housing 20 wherein cam bar 59 is operably coupled with a jaw drive assembly (not explicitly shown) of the actuation assembly of housing 20 to enable selective actuation of end effector assembly 40 to grasp tissue therebetween and apply a closure force within an appropriate jaw closure force range.

To assemble end effector assembly 40, knife blade 78b is inserted through knife channel 74 of second jaw member 44 via slot 86 in surface feature 84, as shown in FIG. 4. With knife blade 78b received in second jaw member 44, first jaw member 42 is operably positioned relative to the second jaw member 44 by positioning distal body portions 64, 66 in opposing relation and positioning proximal flange portion 60 of first jaw member in gap 82 defined between first and second proximal flange portions 62a, 62b of second jaw member 44, as shown in FIG. 5. The distal end portion 90 of cam bar 59 is then passed distally through clevis 32 and the cam pin 55 of cam bar 59 is received in curved cam slot 80 of first jaw member 42, as shown in FIG. 6. The electric wires 99a, 99b and knife rod 78a are guided from the first and second jaw members 42, 44 proximally through the clevis 32.

The clevis 32 is about the jaw members 42, 44, whereby the proximal flange portion 60 of the first jaw member 42 is received proximally through the elongate slots 50, 52 defined in the clevis 32 and the proximal flange portions 62a, 62b of the second jaw member 44 are positioned on support surfaces defined within clevis 32. Upon positioning the clevis 32 about the first and second jaw members 42, 44, the cam pin 55 of the cam bar 59 may be received in the linear slot 54 of the clevis 32. Pivot pin 58 (FIG. 3) may then be passed through the opening 56 in the first side wall 32c of the clevis 32, then into proximal flange portions 60, 62 of first and second jaw members 42, 44 and through the opening (not explicitly shown) in the second side wall 32d of clevis 32 to operably couple the first and second jaw members 42, 44 and the clevis 32 to one another. In aspects, pivot pin 58 may be first passed through second side wall 32d and then through first side wall 32c. Second jaw member 44 may further be secured to clevis 32, e.g., via welding of proximal flange portion 62 to clevis 32, or in any other suitable manner. Opposed slots 33 defined within side walls 32c, 32d (only slot 33 of side wall 32c is shown), for example, may provide access to facilitate welding proximal flange portions 62 to clevis 32, although other configurations are also contemplated.

Turning to FIG. 7, robotic surgical system 500 is configured for use in accordance with the present disclosure. Aspects and features of robotic surgical system 500 not germane to the understanding of the present disclosure are omitted to avoid obscuring the aspects and features of the present disclosure in unnecessary detail.

Robotic surgical system 500 generally includes a plurality of robot arms 502, 503; a control device 504; and an operating console 505 coupled with control device 504. Operating console 505 may include a display device 506, which may be set up in particular to display three-dimensional images; and manual input devices 507, 508, by means of which a person, e.g., a surgeon, may be able to telemanipulate robot arms 502, 503 in a first operating mode. Robotic surgical system 500 may be configured for use on a patient 513 lying on a patient table 512 to be treated in a minimally invasive manner. Robotic surgical system 500 may further include a database 514, in particular coupled to control device 504, in which are stored, for example, pre-operative data from patient 513 and/or anatomical atlases.

Each of the robot arms 502, 503 may include a plurality of members, which are connected through joints, and a mounted device which may be, for example, a surgical tool "ST." One or more of the surgical tools "ST" may be instrument 10 (FIG. 1), thus providing such functionality on a robotic surgical system 500.

Robot arms 502, 503 may be driven by electric drives, e.g., motors, connected to control device 504. Control device 504, e.g., a computer, may be configured to activate the motors, in particular by means of a computer program, in such a way that robot arms 502, 503, and, thus, their mounted surgical tools "ST" execute a desired movement and/or function according to a corresponding input from manual input devices 507, 508, respectively. Control device 504 may also be configured in such a way that it regulates the movement of robot arms 502, 503 and/or of the motors.

It will be understood that various modifications may be made to the aspects and features disclosed herein. Therefore, the above description should not be construed as limiting, but merely as exemplifications of various aspects and features. Those skilled in the art will envision other modifications within the scope and spirit of the claims appended thereto.

What is claimed is:

1. An end effector assembly of a robotic surgical instrument, the end effector assembly comprising:
    a clevis having a proximal end configured to attach to a shaft assembly of the robotic surgical instrument, the clevis including a first side wall, an upper wall having a cut-out, and a second side wall opposite the first side wall and defining a linear slot;
    a first jaw member including a distal body portion, and a proximal flange portion extending proximally from the distal body portion, the proximal flange portion configured to move within the cut-out, the proximal flange portion defining an angled cam slot configured for receipt of a cam pin, the cam pin configured to move longitudinally through the angled cam slot defined by the proximal flange portion and the linear slot defined by the second side wall; and
    a second jaw member including a distal body portion, and at least one proximal flange portion extending proximally from the distal body portion of the second jaw member and received between the first and second side walls, wherein the proximal flange portion of the first jaw member and the at least one proximal flange portion of the second jaw member are pinned to each other such that at least one of the first or second jaw members is configured to pivot relative to the other between a closed state in which the first and second jaw members are closer to one another, and an open state in which the first and second jaw members are further apart from one another.

2. The end effector assembly according to claim 1, wherein the at least one proximal flange portion of the second jaw member includes a first proximal flange portion, and a second proximal flange portion spaced laterally from the first proximal flange portion to define a gap between the first and second proximal flange portions, the proximal flange portion of the first jaw member disposed in the gap.

3. The end effector assembly according to claim 1, wherein the proximal flange portion of the first jaw member extends further proximally than the at least one proximal flange portion of the second jaw member.

4. The end effector assembly according to claim 1, wherein the clevis is configured to prevent rotation of the second jaw member relative to the clevis.

5. The end effector assembly according to claim 1, further comprising a cam bar having a distal end portion received in the clevis, wherein the distal end portion of the cam bar supports the cam pin thereon.

6. The end effector assembly according to claim 1, further comprising a knife blade, wherein the distal body portion of each of the first and second jaw members defines a longitudinally-extending knife channel configured for passage of the knife blade.

7. The end effector assembly according to claim 6, wherein the second jaw member has a surface feature supported on a proximal end of the distal body portion of the second jaw member and protruding toward the first jaw member, the surface feature defining a slot having the knife blade received therein when the knife blade is in a proximal position.

8. A robotic surgical instrument, comprising:
    a housing configured to be operably coupled to a surgical robotic arm;
    a shaft assembly extending distally from the housing; and
    an end effector assembly including:
        a clevis having a proximal end coupled to a distal end portion of the shaft assembly and configured to articulate relative thereto, the clevis including a first side wall, an upper wall having a cut-out, and a second side wall opposite the first side wall and defining a linear slot;
        a first jaw member including a distal body portion, and a proximal flange portion extending proximally from the distal body portion, the proximal flange portion configured to move within the cut-out, the proximal flange portion defining an angled cam slot configured for receipt of a cam pin, the cam pin configured to move longitudinally through the angled cam slot defined by the proximal flange portion and the linear slot defined by the second side wall; and
        a second jaw member including a distal body portion, and at least one proximal flange portion extending proximally from the distal body portion of the second jaw member and received in the clevis, wherein the proximal flange portion of the first jaw member and the at least one proximal flange portion of the second jaw member are pinned to each other such that at least one of the first or second jaw members is configured to pivot relative to the other between a closed state in which the first and second jaw members are closer to one another, and an open state in which the first and second jaw members are further apart from one another.

9. The robotic surgical instrument according to claim 8, wherein the at least one proximal flange portion of the second jaw member includes a first proximal flange portion, and a second proximal flange portion spaced laterally from the first proximal flange portion to define a gap between the first and second proximal flange portions, the proximal flange portion of the first jaw member disposed in the gap.

10. The robotic surgical instrument according to claim 8, wherein the proximal flange portion of the first jaw member extends further proximally than the at least one proximal flange portion of the second jaw member.

11. The robotic surgical instrument according to claim 8, wherein the clevis is configured to prevent rotation of the second jaw member relative to the clevis.

12. The robotic surgical instrument according to claim 8, further comprising a cam bar having a distal end portion received in the clevis, wherein the distal end portion of the cam bar supports the cam pin thereon.

13. The robotic surgical instrument according to claim 8, further comprising a knife blade, wherein the distal body portion of each of the first and second jaw members defines a longitudinally-extending knife channel configured for passage of the knife blade.

\* \* \* \* \*